United States Patent [19]

Hecht et al.

[11] 4,387,338

[45] Jun. 7, 1983

[54] METHOD AND APPARATUS FOR TESTING A METALLIC WORKPIECE BY INDUCING EDDY CURRENTS THEREIN

[75] Inventors: Hans Hecht, Stuttgart; Peter Neumaier, Reutlingen, both of Fed. Rep. of Germany

[73] Assignee: Institut Dr. Friedrich Forster Prüfgerätebau, Reutlingen, Fed. Rep. of Germany

[21] Appl. No.: 134,495

[22] Filed: Mar. 27, 1980

[30] Foreign Application Priority Data

Apr. 3, 1979 [DE] Fed. Rep. of Germany ....... 2913291

[51] Int. Cl.³ ..................... G01N 27/72; G01R 33/12
[52] U.S. Cl. ..................................... 324/236; 324/225
[58] Field of Search ............... 324/225, 226, 227, 232, 324/236, 237, 238; 331/65

[56] References Cited

U.S. PATENT DOCUMENTS 3,449,661  6/1969  Puidak .................................. 324/237
4,204,160  5/1980  Voll ....................................... 331/65

Primary Examiner—Gerard R. Strecker
Assistant Examiner—Walter E. Snow
Attorney, Agent, or Firm—George J. Netter

[57] ABSTRACT

A method for testing a metallic workpiece by eddy currents induced by a test coil in the workpiece, in which a measured variable that is a function of the test coil impedance serves as a measure for workpiece physical properties. The circuit includes an oscillator with an amplifier and two resonant circuits adjusted to neighboring frequencies $f_1$, $f_2$, the test coil impedance is at least part of the inductive component of one or both resonant circuits and a variable component influences the resonant frequency of one of the resonant circuits.

20 Claims, 6 Drawing Figures

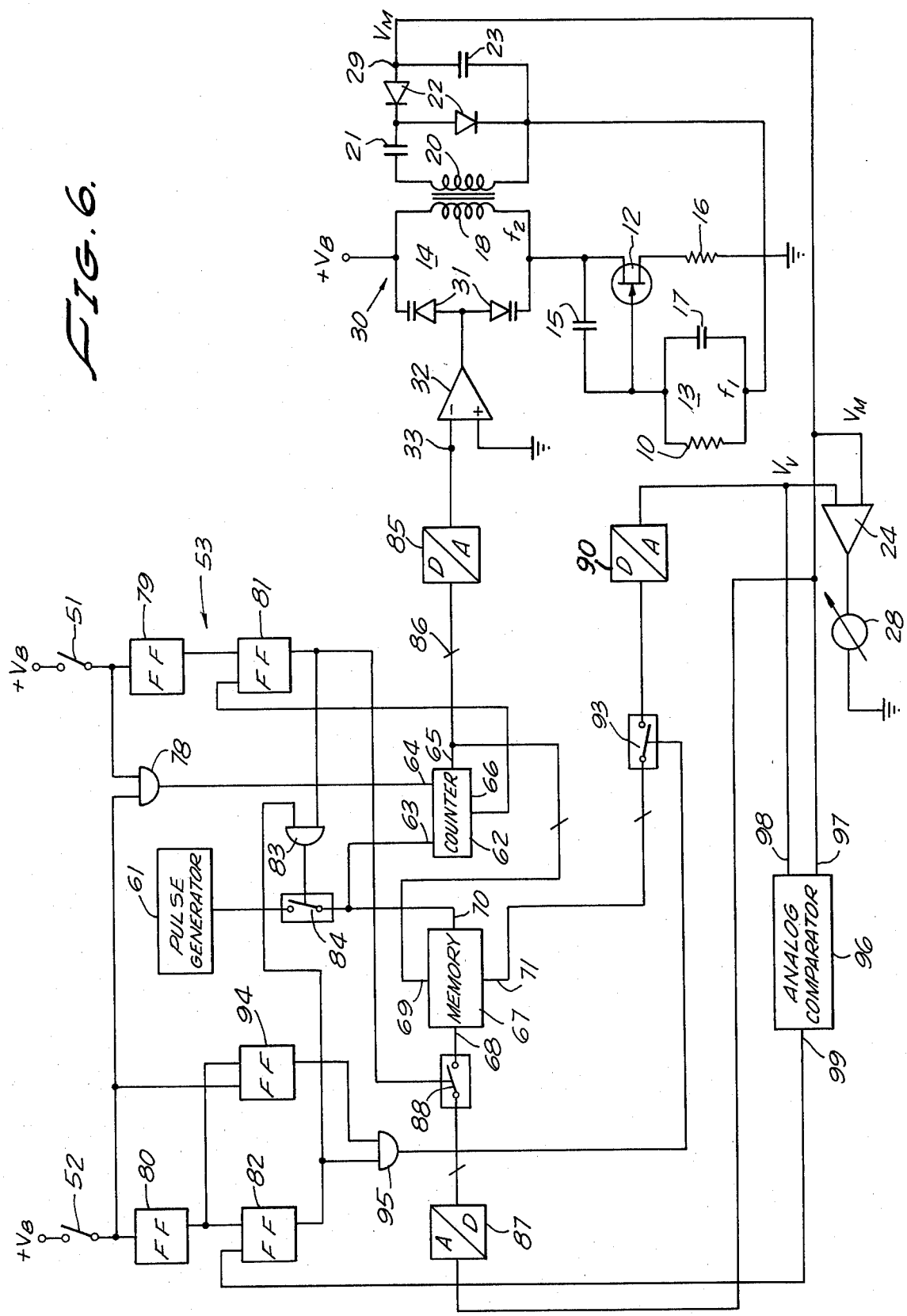

METHOD AND APPARATUS FOR TESTING A METALLIC WORKPIECE BY INDUCING EDDY CURRENTS THEREIN

The present invention relates to a method for testing a metallic workpiece by means of eddy currents induced by a test coil in the workpiece, wherein a measured variable is determined which is a function of the test coil impedance and which serves as a measure for workpiece physical properties. Further, the invention relates to apparatus for carrying out the method having a test coil suitable for generating eddy currents in the workpiece, and an electric circuit arrangement for producing a measured variable which is a function of the impedance of the test coil, consisting of an oscillator circuit with an amplifier and two resonant circuits adjusted to neighboring frequencies $f_1$, $f_2$, wherein the impedance of the test coil constitutes fully or partly the inductive component of one of two or of both resonant circuits and wherein a variable component is provided which influences the resonant frequency of one of the two resonant circuits.

The method to be described herein is used, for instance, for testing metallic semi-finished products and finished products for the presence of defects, such as cracks and marks, for electric conductivity and magnetic permeability and for physical properties related with the two latter properties, such as hardness and the like. For determining the measured variable which is a function of the impedance of the test coil, conventional measuring circuits, such as electric bridge circuits, and oscillator circuits are used, in which the test coil forms part of a resonant circuit. In the last-mentioned case, the measured variable may consist of the oscillating voltage or frequency of the oscillator. From U.S. Pat. No. 3,449,661, for example, an oscillator circuit has been known in which a first resonant circuit has an inductive component consisting of the inductivity of the test coil applied to the grid of a vacuum tube, while a second resonant circuit is applied to the plate of the tube. Frequently difficulties are encountered in that the measured variable changes when the position of the test coil relative to the workpiece is varied, which may result when a scanning test coil is by chance moved closer or farther away from the surface of the workpiece. In the case of the cited U.S. patent, this difficulty is largely eliminated by the fact that the resonant frequency and the quality of the plate resonant circuit are set to a value where the oscillator voltage varies only slightly or not at all between the lifted-off and applied condition of the scanning test coil. This is achieved by incrementally varying the inductivity of the resonant circuit and a resistance connected in parallel to the resonant circuit, while alternately lifting-off and applying the scanning test coil from and to the test coil, until there is no noticeable variation of the oscillator voltage between the lifted-off and applied condition of the scanning test coil. However, this is a rather lengthy and extraordinarily time-consuming balancing process which greatly reduces the value of the described test arrangement. The same applies analogously to other test arrangements, also.

SUMMARY OF THE INVENTION

In accordance with the present invention, there are provided eddy current defect determining method and apparatus wherein balancing of the system to obtain the least possible variation of the measured variable with changing positions of the test coil in relation to the workpiece can be effected easily, rapidly and conveniently. The previous practice of balancing the system to achieve the least possible variation of the measured variable with changing positions of the test coil in relation to the workpiece has been greatly simplified in this invention. While in the prior art methods it was necessary to change several times between a first and a second position of the test coil in relation to the workpiece, i.e., in the case of a scanning test coil to change several times between the lifted-off and the applied condition of the test coil, and to operate each time two control elements while observing at the same time a measuring instrument (e.g., voltmeter), the method and apparatus described herein requires only one change between the first and the second position of the test coil and the change of only one parameter. According to further advantageous aspects of the invention, the balancing procuedure is still further simplified and largely automated.

DESCRIPTION OF THE DRAWING

FIGS. 5 and 6 depict schematic block diagrams of further embodiments of the invention.

DESCRIPTIONS OF PREFERRED EMBODIMENTS

Figure 1:
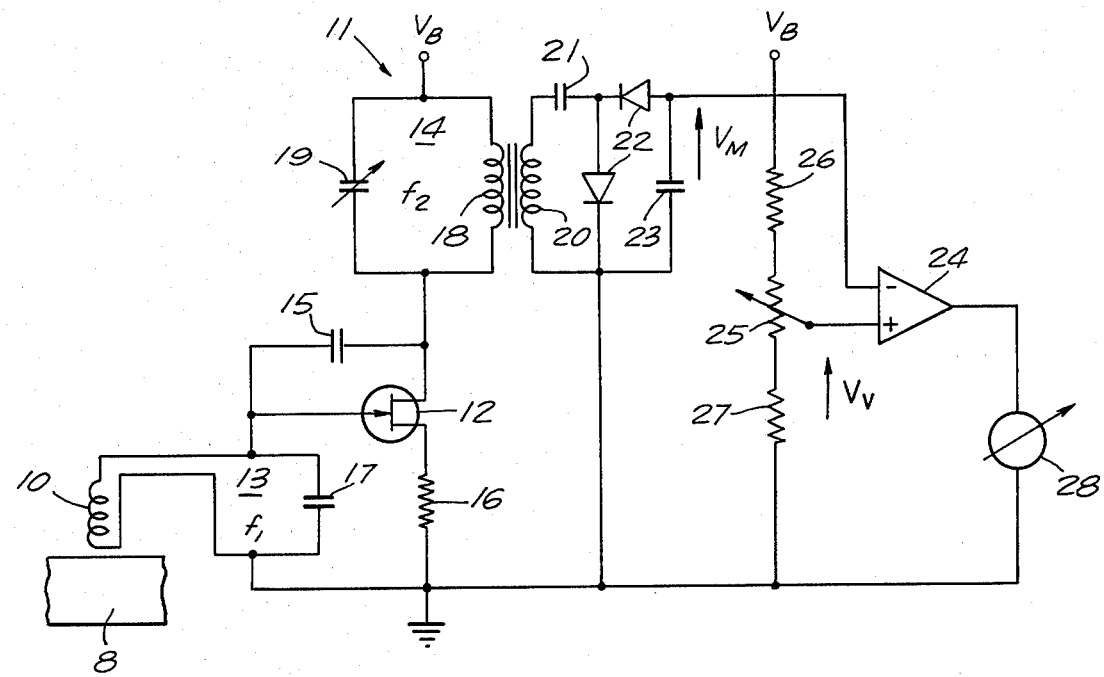
FIG. 1 shows test apparatus arrangement of the prior art.

FIG. 1 shows the schematic wiring diagram of known test apparatus for determining the presence of defects in metallic workpieces, which, similar to U.S. Pat. No. 3,449,661, uses an oscillator circuit 11 for deriving a measured variable, namely, the oscillator voltage $V_M$, corresponding to the impedance of a scanning test coil 10. The oscillator circuit 11 comprises a field-effect transistor 12 as amplifier element and two resonant circuits 13 and 14 adjusted to the respective frequencies $f_1$ and $f_2$, a reaction capacitor 15 and the resistor 16. For the two resonant frequencies $f_1$, $f_2$, closely neighboring frequencies are generally selected. The resulting oscillating frequency of the oscillator circuit 11 is lower than the lower one of the two frequencies $f_1$, $f_2$.

The resonant circuit 13 consists of the test coil 10 and a capacitor 17 connected in parallel therewith, and the resonant circuit 14 consists of the inductor 18 and a variable capacitor 19 connected in parallel therewih. The inductor 18 includes a secondary winding 20 to which a rectifier circuit is connected via a coupling capacitor 21. The rectifier circuit includes two diodes 22 and a charging capacitor 23. The rectified oscillator voltage $V_M$ is applied to a first input of a differential amplifier 24, while the second input of the latter is connected to the wiper of a potentiometer 25 which together with the resistors 26 and 27 forms a voltage divider for the supply voltage $V_B$. The output current of the amplifier 24 is measured by an indicating instrument 28. There exists a functional relationship between the resulting oscillator voltage $V_M$ and the impedance of the test coil 10. If the latter is applied to a metallic workpiece 8, the oscillator voltage $V_M$ depends on the material properties of the workpiece, because of the reaction of the test coil 10 to the eddy currents produced in the workpiece. In the present case, only those changes of the eddy-current reactions are to be determined which are produced by defects in the workpiece, the difference formed in the amplifier 24 between the oscillator voltage $V_M$ and an adjustable divider voltage $V_V$ is displayed by the indicating instrument 28. This is achieved by finding a setting of the variable capacitor 19 at which the ocillator voltage $V_M$ and, thus, the display of the indicating instrument 28, does not change between the applied and the lifted-off condition of the test coil 10 in relation to the workpiece 8. Considering, however, that any setting of the variable capacitor 19 will result in a different oscillator voltage $V_M$, it will be necessary with a view to maintaining the balanced condition at the indicating instrument 28, to reset the potentiometer 25 every time the setting of the variable capacitor is changed, so as to obtain also a new divider voltage $V_V$. Accordingly, the desired setting of the two control elements can be found only by stepwise approximation. This will be explained in more detail hereafter with reference to FIGS. 2 and 3.

Figure 2:
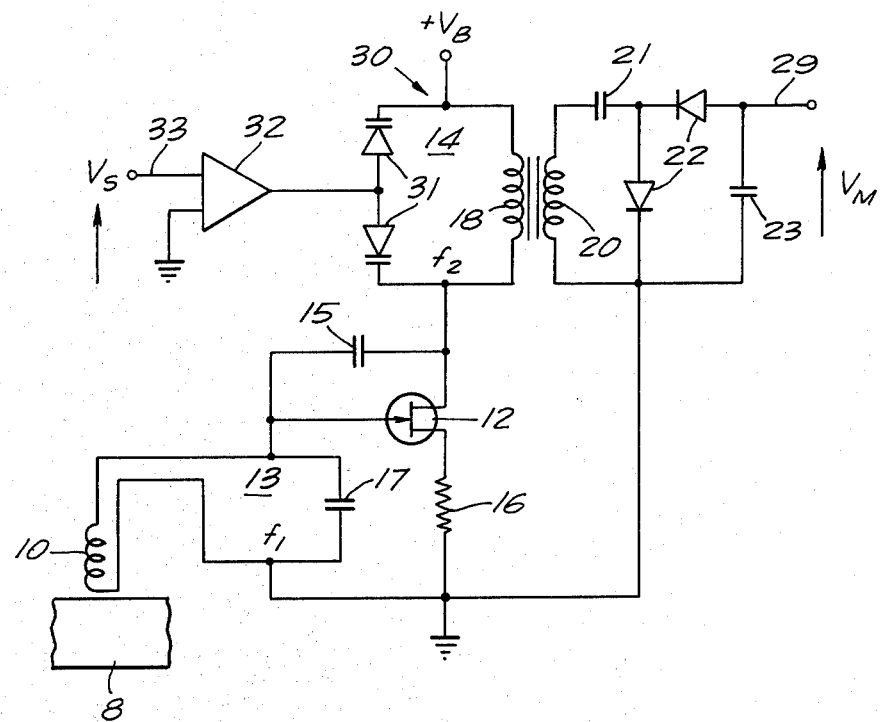
FIG. 2 shows part of test apparatus arrangement in accordance with the invention.

FIG. 2 shows an oscillator circuit 30 corresponding in many respects to the oscillator circuit 11 shown in FIG. 1 so that most of the reference numbers of FIG. 1 can be used here, too. Instead of the variable capacitor 19, however, two reactance diodes 31 connected in series are provided, the capacitance of which is controlled by voltage $V_S$ at the input of an operational amplifier 32. The series connection of the reactance diodes serves to increase the modulation range of the diodes through the applied AC voltage.

Figure 3:
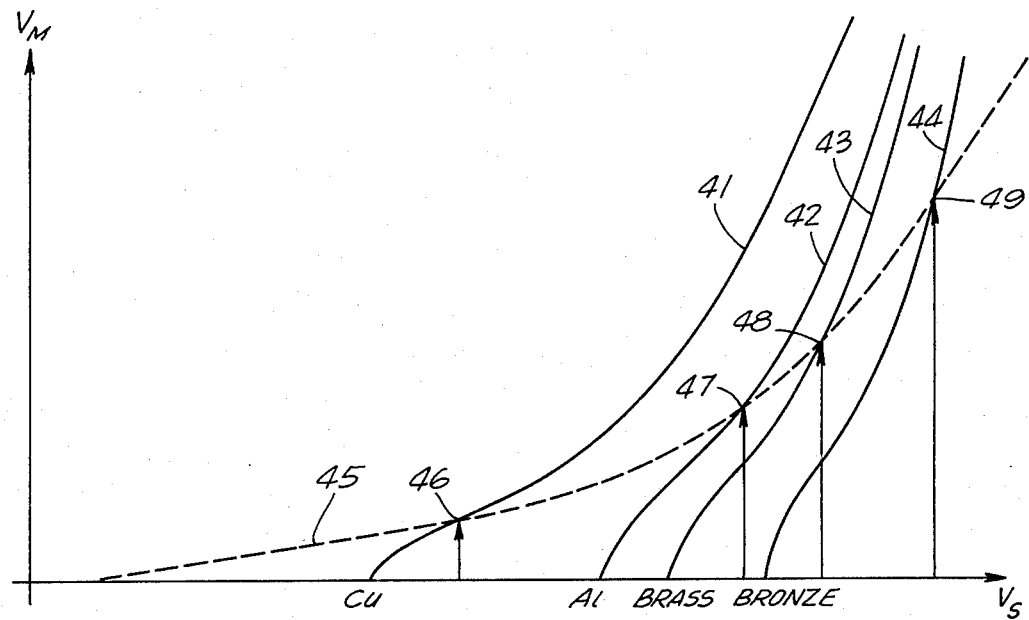
FIG. 3 is a graph of the oscillator voltage $V_M$.

FIG. 3 shows the oscillator voltage $V_M$ obtained as a function of the control voltage $V_S$, i.e., as a function of the resonant frequency $f_2$ of the circuit 14 for a number of different conductivities of the workpiece. For copper, aluminum, brass or bronze, the curves 41 to 44 are obtained with the test coil 10 always fully applied to the workpiece 8. If, however, the test coil 10 is completely lifted-off the workpiece 8, the dotted curve 45 is obtained which cuts the curves 41 to 44 at the respective points 46 to 49. The points of intersection 46 to 49 correspond to the values of the control voltage $V_S$ or the resonant frequency $f_2$ for which conformity of the oscillator voltage $V_M$ can be obtained in the lifted-off and applied condition of the test coil 10. The relatively large differences between the $V_M$ values associated with the points of intersection 46 to 49 give an idea of how much the divider in FIG. 1 has to be adjusted in order to obtain a suitable $V_V$ value.

Figure 4:
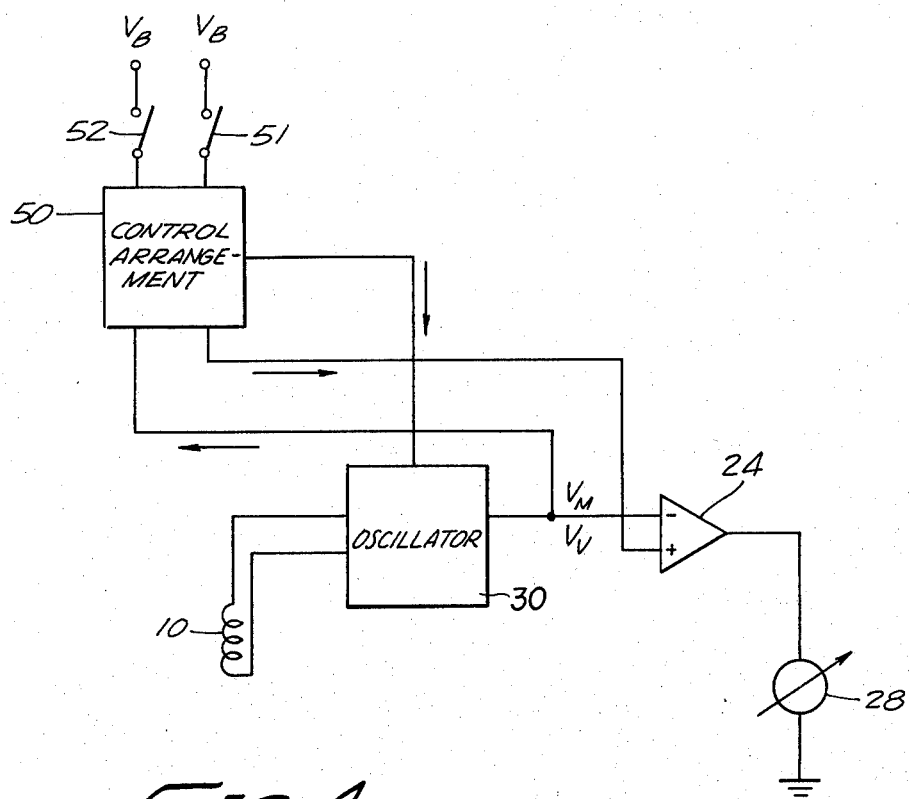
FIG. 4 shows a schematic block diagram of apparatus of the invention.

FIG. 4 depicts the principles of the invention by means of a block diagram. An oscillator circuit 30 corresponding to that shown in FIG. 2, for example, has been used here as one of several possible circuits for developing a meausred variable $V_M$ functionally corresponding to the impedance of the test coil 10. The measured variable $V_M$ is applied on the one hand to one of the two inputs of a differential amplifier 24 the output of which feeds the indicating instrument 28, and on the other hand to one input of a control arrangement 50 which will be described in more detail below. A first output of the control arrangement 50 is connected to the control input of oscillator circuit 30, and a second output of the control arrangement is connected to the second input of the amplifier 24. In addition, the control arrangement 50 includes two setting inputs into which setting signals are supplied via input switches 51 and 52.

The operation of the FIG. 4 arrangement is as follows. When the test coil 10 has been lifted off the workpiece, a first setting signal is supplied into the control arrangement 50 via the input switch 51. This initiates in the control arrangement 50 the building-up of a continuously varying control value, namely, the voltage $V_S$, which modulates a test parameter, in the present case a resonant frequency $f_2$ of the oscillator circuit 30. The measured variable, namely, the oscillator voltage $V_M$, in turn, varies as a function of the test parameter. It is stored in the control arrangement 50 in a two-coordinate memory the second coordinate of which is modulated by the control voltage $V_S$. Therefore, the measured variable $V_M$ is stored as a function of the test parameter $f_2$. Now, the test coil 10 is brought into contact with the workpiece and the second input switch 52 is operated. Again, a continuously varying control voltage $V_S$ is built up in the control arrangement 50 which acts to vary the oscillator voltage $V_M$. The oscillator voltage $V_M$ and the oscillator voltage previously stored are synchronously supplied to the inputs of a comparator which when conformity between the signals at its inputs is reached emits a signal which stops operation of the memory and interrupts the control voltage. Thus, the point of intersection between two functions is determined and stored, namely, according to FIG. 3 the point of intersection between the function 45 and one of the functions 41 to 44. Such points of intersection (46–49) can be directly employed for measuring an unknown conductivity. In this case, both the oscillator voltage $V_M$ present at the point of intersection and the associated control voltage $V_S$ are a measure of the conductivity value. If, however, not the absolute value of material physical property, but rather its local differences, in the present case the differences in the conductivity, or inhomogeneities caused by defects are to be determined, the point of intersection between the two functions not only provides the test parameter $V_S$ necessary to provide optimum compensation for the different positions of the test coil, but also, the comparative value $V_V$ for the oscillator voltage $V_M$ required for the zero adjustment of the indicating instrument is now provided.

Figure 5:
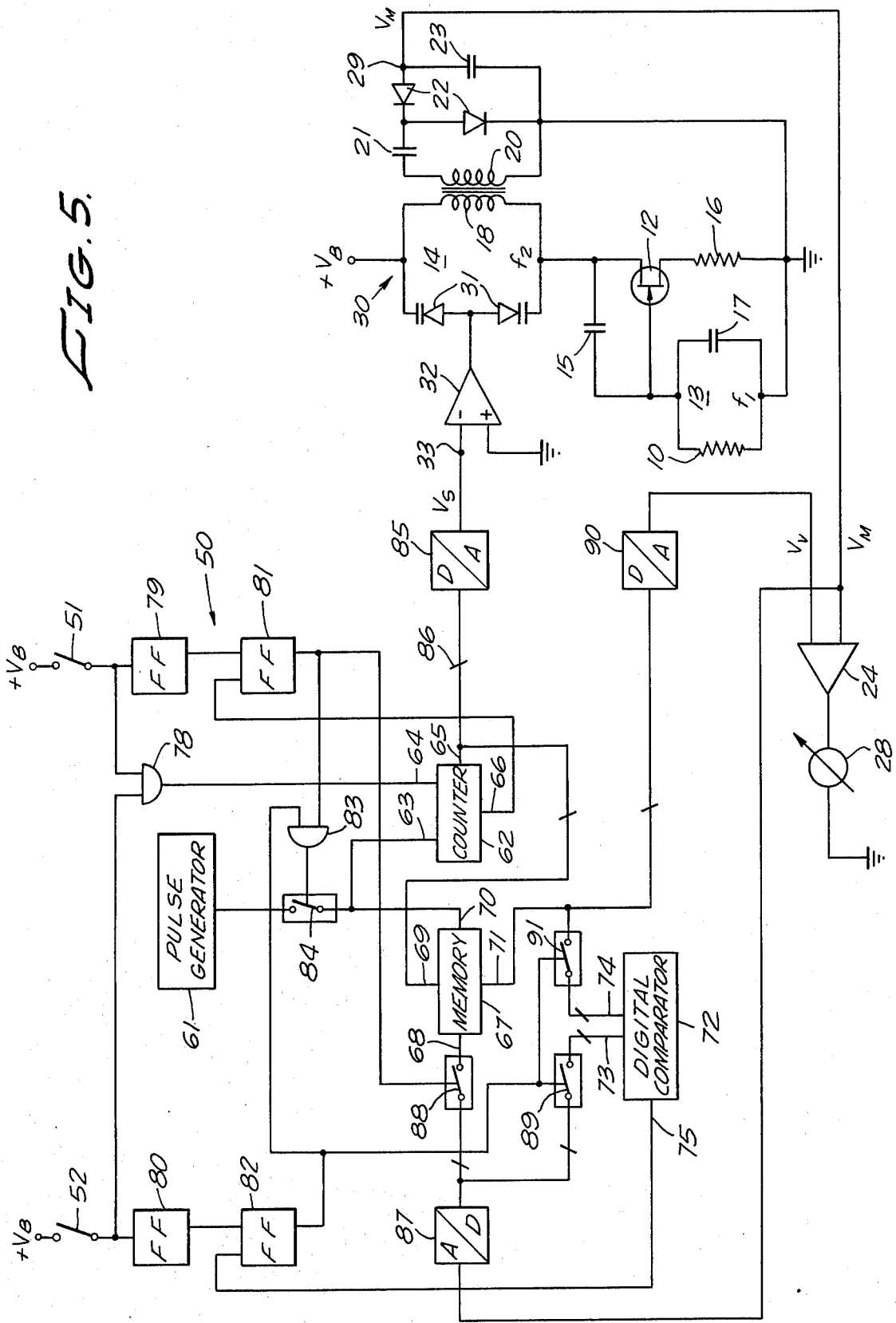

FIG. 5 shows an example of a control circuit 50. The oscillator 30 corresponds in all details to that shown in FIG. 2 so that it need not be described in detail. The oscillator voltage $V_M$ at the output 29 and a comparative voltage $V_V$ are applied to the first and second inputs of the differential amplifier 24, and the output of the latter is rendered by the indicating instrument 28.

The major components of the control circuit 50 are a pulse generator 61 producing a continuous sequence of counting pulses; a counter 62 having a counting input 63, a reset input 64, a counted-value output 65 and an overflow output 66 and which in the present example has a capacity of for instance 8 bits; a read-write memory 67 which in the present example has a resolution of 8 bits with 256 storage locations and including a data input 68, an address input 69, a pulse input 70 and a data output 71; and a digital comparator 72 having two inputs 73, 74 and one output 75. Two input switches 51, 52 are connected via an OR-gate 78 to the reset input 64 of the counter 62, and with the inputs of two monostable flip-flops 79, 80, which have their inputs, in turn, connected to the setting inputs of two bistable flip-flops 81, 82. The outputs of flip-flops 81, 82 are connected via OR-gate 83 with the control input of an electronic switch 84, for instance a field-effect transistor, which in turn enables the pulse generator 61 to be connected to the counting input 63 of the counter 62 and to the pulse input 70 of the memory 67. The overflow output 66 of counter 62 is connected to the reset input of bistable flip-flop 81, and additional lines lead from the counted-value output 65 of the counter via a digital-to-analog converter 85 to the control input 33 of the oscillator circuit 11, and directly to the address input 69 of the memory 67. The line between the counter 62 and the digital-to-analog converter 85 has been marked by a line 86 to indicate that there (as well as elsewhere) there are a number of lines, that is, there is a group of digital lines for transmitting 8 bits. The output 29 of oscillator 30 is connected with the input of an analog-to-digital converter 87, the output of which is connected via two electronic switches 88, 89 with the data input 68 of memory 67 and with the input 73 of the digital comparator 72, respectively. The memory data input 71 connects via a digital-to-analog converter 90 to the second input of differential amplifier 24 and via an electronic switch 91 with the input 74 of the digital comparator 72. The control inputs of the electronic switches 89, 91 are connected with the output of the bistable flip-flop 82, and the control input of the switch 88 interconnects the output of the bistable flip-flop 81. The digital comparator output 75 interconnects with the reset input to the bistable flip-flop 82.

The circuit described in the immediately preceding paragraph operates as follows: To begin with, the switch 51 is closed with the test coil 10 in the lifted-off position relative to the workpiece. The leading edge of the input pulse produced thereby acts to reset the counter 62 via OR-gate 78 and to pick up the monostable flip-flop 79. At the end of the time delay of this flip-flop, the trailing edge of its output pulse sets the bistable flip-flop 81 which, in turn, applies the clock frequency pulses of the pulse frequency generator 61 via the OR-gate 83 and the switch 84 to the counting input 63 of the counter 62 and to the pulse input 70 of the memory 67, while simultaneously connecting to the data input 68 of the memory 67 via switch 88, the measured variable of the oscillator circuit 30, which has been converted into a digital value in the analog-to-digital converter 87. As the counted value obtained at the output 65 of the counter 62 continues, a correspondingly varying analog control voltage $V_S$ is obtained at the output of the digital-to-analog converter 85, which control voltage $V_S$ varies the capacitance value of the diodes 31 within the given range and, thus, the resonant frequency $f_2$ of the resonant circuit 14.

The digital value corresponding to the oscillator voltage $V_M$ obtained at the output of the analog-to-digital converter 87 as a function of the control voltage $V_S$, is stored in the memory 67, while the storage addresses likewise varying as a function of $V_S$ (i.e., $V_M = f(V_S)$). The storage process is completed by an overflow pulse received from the counter 62 which resets the bistable flip-flop 81, stops the clock pulses to the counter 62 and to the memory 67, and terminates the variation of the control voltage $V_S$. The second step of the balancing process is initiated by connecting the test coil 10 with the workpiece, for instance by moving the test coil into contact with the workpiece, and by momentarily closing the switch 52. The counter 62 is reset via the OR-gate 78 and, following a delay caused by the monostable flip-flop 80, the bistable flip-flop 82 is set. The latter starts the counting process in the counter 62 via the OR-gate 83 and the switch 84 and initiates, via the digital-to-analog converter 85, the building-up of the continuously varying control voltage $V_S$ which varies the resonant frequency $f_2$ of the oscillator circuit 30 in the same manner as described before. The setting of the bistable flip-flop 82 connects the output of the analog-to-digital converter 87 via the switch 89 with the comparator input 73, and the data output 71 via the switch 91 and the input 74 of the digital comparator 72. The memory 67 receives addresses from the counter 62 and clock pulses from the pulse generator 61, via switch 84. Therefore, two values are supplied to the inputs 73, 74 of the digital comparator 72, one corresponding to the oscillator voltage $V_M$, with the workpiece in contact with the test coil 10, and the other corresponding to the oscillator voltage $V_M$ with the workpiece lifted off the test coil 10, both being similarly a function of the control voltage $V_S$. At the moment where conformity is reached between the two input values, i.e., where one of the points of intersection 46 to 49 of FIG. 3 is reached or exceeded, a signal is obtained at the digital comparator output 75 which resets the bistable flip-flop 82, thereby terminating the comparison of the two functions. The counter 62 is now no longer supplied with clock pulses, the counted value reached at the output 65 and, thus, the control voltage $V_S$ corresponding to that value and the associated resonant frequency $f_2$ are maintained. As the address at the input 70 of the memory 67 no longer varies, the measured variable present at the data output 71 at the moment when conformity between the two functions is reached is likewise retained and available, after conversion into an analog value, for further test functions, as comparative value $V_V$. If, for instance, following the process just described, a scanning test coil 10 passes over a flaw in the workpiece, the oscillator voltage $V_M$ will vary, while the comparative voltage $V_V$ remains constant. The flaw is indicated by a deflection of the pointer of the indicating instrument 28.

The control circuit 53 used in FIG. 6 differs from the control circuit 50 mainly in that an analog comparator 96, i.e., a simple comparator, is used instead of the digital comparator 72. This analog comparator has its two inputs 97, 98 connected to the output 29 of the oscillator circuit 30 and to the output of the digital-to-analog converter 90, respectively. Its output 99 is connected with the reset input of bistable flip-flop 82. The latter has connected in parallel to its input end a further bistable flip-flop 94 which has its reset input connected to the switch 52. The output of the flip-flop 82 is connected with the OR-gate 83 and the outputs of both flip-flops 82 and 94 are connected via an OR-gate 95 with an electronic switch 93 connected between the data output 71 of the memory 67 and the input of the digital-to-analog converter 90. The two switches 89 and 91 of the FIG. 5 embodiment do not exist in this arrangement.

Operation of the control circuit 53 corresponds largely to that of the control circuit 50. As described before, a digital value corresponding to the oscillator voltage $V_M$ is stored in the memory 67 as a function of the control voltage $V_S$, in the lifted-off position of the test coil 10. Upon receipt of a signal from the input switch 52, the counter 62 as well as the bistable flip-flop 94 are reset, with the test coil 10 in contact with the workpiece. At the end of the time delay of the monostable flip-flop 80, the building-up of the continuously varying control voltage $V_S$ is initiated in the known manner via OR-gate 83 and the switch 84. At the same time, the two bistable flip-flip 82 and 94 are set, and their output signal closes the switch 93 via OR-gate 95. As a result, the measured variable stored in the memory is supplied to the input 98 of the analog comparator 96, via the digital-to-analog converter 90, while the measured variable $V_M$ taken directly from the oscillator circuit 30 is applied to the input 97 of the analog comparator 96. The latter compares the approximating measured variables received at its inputs and emits a signal at its output 99 when conformity between the two measured variables is obtained. This signal resets the bistable flip-flop 82, thus stopping the comparison via the OR-gate 83 and the switch 84. The switch 93 remains, however, closed via the OR-gate 95 and the bistable flip-flop 94 so that the measured variable received at the output of the digital-to-analog converter 90 is maintained as comparative voltage $V_V$ at the input of the differential amplifier 24 and so that the testing operation can be started as described above. Besides, the use of two input switches 51, 52, is not absolutely necessary. Rather, a test circuit could also be imagined in which one single input switch 51 would start the first balancing step, i.e., the storing of the measured variable obtained with the test coil lifted off the workpiece, and in which upon termination of the counting cycle of the counter 62 the overflow output 66 would cause the input switch 51 to be switched over to the second supply input, i.e., to the input of the monostable flip-flop 80, so that a second operation of the input switch 51 would initiate the comparison of the two measured variables.

It goes without saying that what has been said above does not only apply to the two extreme conditions, namely, "test coil completely lifted off the workpiece" and "test coil fully in contact with the workpiece," but that the comparison of the two functions can be carried out also for all conditions between these two extreme conditions. In the case of scanning test coils, for instance, the liftoff compensation can be most efficiently carried out in many cases by a comparison between the two conditions "test coil separated from the workpiece by the thickness of a non-conductive intermediate layer" and "test coil directly applied to the workpiece." On the other hand, the use of the invention is by no means restricted to scanning test coils. Rather, it may also be employed, for instance, in the case of encircling test coils for compensating the so-called wobble effect, which term describes variations of the measured variables as a function of positional changes of the workpiece vertically to the direction of movement through the encircling coil. In this case, it is necessary only to realize two representative conditions. The examples described above always use an oscillator arrangement for deriving a measured variable from the impedance of the test coil. Although an oscillator arrangement is particularly suited for the application of the invention, it is by no means the only arrangement possible. Rather, the application can be conveniently used in all arrangements, in which when two different geometrical relationships exist between the test coil and the workpiece, the measured variable depends on a test parameter in accordance with two different functions and in which these functions intersect each other in at least one point.

We claim:

1. A method for testing a metallic workpiece in which a test coil generates eddy currents in the workpiece, and a measured variable functionally related to the test coil impedance is determined which serves as a measure for material physical properties of the workpiece, comprising:

arranging the test coil and workpiece into a first geometrical relationship;

continuously varying a circuital parameter throughout a predetermined range;

storing and recording first values of the measured variable which are a function of the circuital parameter;

arranging the test coil and workpiece into a second geometrical relationship;

continuously varying the circuital parameter throughout the same range, and storing and recording second values of the measured variable which are a function of the circuital parameter, all while maintaining the second geometric relationship;

comparing the first stored values with the second stored values;

determining the particular circuital parameter and the particular first or second stored values functionally related to the said parameter such that the stored values being compared with one another are in conformity; and utilizing one of the first or second stored values as a comparison voltage for comparison with other digital values of the measured variable functionally related to the particular circuital parameter.

2. A method as in claim 1, including the further step of storing the measured variable determined on comparison conformity.

3. A method as in claim 2, which includes deriving the difference between the measured variable obtained from time to time and the previously stored measured variable.

4. A method as in claim 1, in which the first geometrical relationship is the condition in which the test coil and the workpiece are spaced from each other, and the second geometrical relationship is the condition in which the test coil and workpiece are in contact with each other.

5. A method as in claim 1, in which the test parameter is the resonant frequency of a resonant circuit the inductive component of which consists at least partly of the test coil.

6. A method as in claim 1, in which the test parameter is the resonant frequency of a resonant circuit and said resonant circuit is part of an oscillator circuit the output values of which are determined by the test coil impedance, one of the said output values constituting said measured variable.

7. A method as in claim 6, in which there are provided two resonant circuits of different resonant frequencies $f_1$ and $f_2$, respectively, the impedance of the test coil constituting a primary component of the resonant circuit having the resonant frequency $f_1$, and the resonant frequency $f_2$ of the second oscillator circuit constituting the measured variable.

8. A method as in claim 1, including converting the measured variable to a digital value prior to storing.

9. A method for testing a metallic workpiece in which a test coil generates eddy currents in the workpiece, and a measured variable functionally related to the test coil impedance is determined which serves as a measure for material physical properties of the workpiece, comprising:

arranging the test coil and workpiece into a first geometrical relationship;

continuously varying a circuital parameter throughout a predetermined range;

storing and recording first digital values of the measured variable which are a function of the circuital parameter;

arranging the test coil and workpiece into a second geometrical relationship;

continuously varying the circuital parameter throughout the same range, and storing and recording second digital values of the measured variable which are a function of the circuital parameter, all while maintaining the second geometric relationship;

comparing the first stored values with the second stored values;

determining the particular circuital parameter and the particular first or second stored values functionally related to the said parameter such that the stored values being compared with one another are in conformity; utilizing one of the first or second stored values as a comparison voltage for comparison with other digital values of the measured variable functionally related to the particular circuital parameter; and continuously controlling the sequence of varying the circuital parameter by accumulating clock pulses in a counter and using the accumulated value as a parameter for the control of the circuital parameter variations.

10. A method as in claim 9, in which the function of the test parameter when the test coil and workpiece are in the first geometrical relationship is converted into a digital value and stored, and the function of the test parameter when the coil and workpiece are in the second geometrical relationship is compared with the stored function.

11. Apparatus for testing a metallic workpiece having a test coil for producing eddy currents in the workpiece, an electric circuit arrangement for producing a measured variable functionally related to the test coil impedance including an oscillator circuit with amplifying means and two resonant circuits adjusted to neighboring frequencies $f_1$ and $f_2$, wherein the impedance of the test coil constitutes at least partially the inductive component of at least one of the resonant circuits and a component of the oscillator circuit varies the resonant frequency of one of the two resonant circuits, comprising:

the component is electrically selectively variable;

a generator for providing a uniformly varying control signal electrically connected to vary said component, said generator including a pulse generator, a counter selectively connected to the pulse generator, and a digital-to-analog converter connected to the output of the counter;

a storage means responsive to the electric control signal and interconnected with the output of the oscillator circuit which includes the measured variable; and a comparator having a first input selectively connected to the output of the oscillator circuit and a second input selectively connected to the output of said storage means, the comparator emitting a signal when the measured variables at its inputs are in conformity.

12. Apparatus as in claim 11, in which the component which influences the resonant frequency $f_2$ consists of at least one voltage variable capacitor.

13. Apparatus as in claim 11, in which switching means are provided for controllably connecting the pulse generator to the counter.

14. Apparatus for testing a metallic workpiece having a test coil for producing eddy currents in the workpiece, an electric circuit arrangement for producing a measured variable functionally related to the test coil impedance including an oscillator circuit with amplifying means and two resonant circuits adjusted to neighboring frequencies $f_1$ and $f_2$, wherein the impedance of the test coil constitutes at least partially the inductive component of at least one of the resonant circuits and a component of the oscillator circuit varies the resonant frequency of one of the two resonant circuits, comprising:

the component is electrically selectively variable;

a generator for providing a uniformly varying control signal electrically connected to vary said component;

a storage means responsive to the electric control signal and interconnected with the output of the oscillator circuit which includes the measured variable, said storage means including a digital read-write memory, having an analog-to-digital converter connected to its data input, and its address input connected to the output of the counter; and a comparator having a first input selectively connected to the output of the oscillator circuit and a second input selectively connected to the output of said storage means, the comparator emitting a signal when the measured variables at its inputs are in conformity.

15. Apparatus for testing a metallic workpiece having a test coil for producing eddy currents in the workpiece, an electric circuit arrangement for producing a measured variable functionally related to the test coil impedance including an oscillator circuit with amplifying means and two resonant circuits adjusted to neighboring frequencies $f_1$ and $f_2$, wherein the impedance of the test coil constitutes at least partially the inductive component of at least one of the resonant circuits and a component of the oscillator circuit varies the resonant frequency of one of the two resonant circuits, comprising:

the component is electrically selectively variable;

a generator for providing a uniformly varying control signal electrically connected to vary said component;

a storage means responsive to the electric control signal and interconnected with the output of the oscillator circuit which includes the measured variable, said storage means including a read-write memory having a data input, a data output and an address input; and switching means for selectively connecting the measure variable to the read-write memory data input; and a comparator having a first input selectively connected to the output of the oscillator circuit and a second input selectively connected to the output of said storage means, the comparator emitting a signal when the measured variables at its inputs are in conformity.

16. Apparatus as in claim 15, in which the comparator is a digital comparator having first input selectively connected via an analog-to-digital converter to the output of the oscillator circuit and a second input selectively connected to the data output of the memory.

17. Apparatus as in claim 15, in which there is provided an analog converter with a first input selectively connectable to the output of the oscillator circuit, and a second input selectively connectable via a digital-to-analog converter to the data output of the memory.

18. Apparatus as in claim 15, in which a first bistable flip-flop has its output connected to a switching means which connects the pulse generator with the counter and the memory and second switching means for selectively connecting the output of the oscillator circuit via a digital-to-analog converter to the data input of the memory;

an overflow output of the counter is connected to the reset input of the first bistable flip-flop;

a second bistable flip-flop having its output connected to third switching means for selectively connecting the pulse generator output with the counter and the memory; and fourth switching means for connecting the data output of the memory with the comparator;

the output of the comparator is connected to the reset input of the second bistable flip-flop; and input switch for setting the first and second bistable flip-flops.

19. Apparatus as in claim 18, in which further flip-flops are provided between the input switches and the first and second bistable flip-flops, respectively.

20. Apparatus as in claim 15, in which a digital-to-analog converter is connected to receive the data output of the memory, said converter having an output connected as a first input to a differential amplifier, the second amplifier input being the output of the oscillator circuit.

* * * * *